(12) United States Patent
Kilsgaard et al.

(10) Patent No.: US 9,918,650 B2
(45) Date of Patent: Mar. 20, 2018

(54) EEG MONITOR WITH CAPACITIVE ELECTRODES AND A METHOD OF MONITORING BRAIN WAVES

(71) Applicant: WIDEX A/S, Lynge (DK)

(72) Inventors: Soren Kilsgaard, Smorum (DK); Mike Lind Rank, Farum (DK); Michael Ungstrup, Allerod (DK); Morten Holm Jensen, Gentofte (DK); Preben Kidmose, Maalov (DK)

(73) Assignee: WIDEX A/S, Lynge (DK)

( * ) Notice: Subject to any disclaimer, the term of this patent is extended or adjusted under 35 U.S.C. 154(b) by 865 days.

(21) Appl. No.: 14/187,705

(22) Filed: Feb. 24, 2014

(65) Prior Publication Data

US 2014/0171775 A1    Jun. 19, 2014

Related U.S. Application Data

(63) Continuation-in-part of application No. PCT/EP2011/064544, filed on Aug. 24, 2011.

(51) Int. Cl.
*A61B 5/0478* (2006.01)
*A61B 5/04* (2006.01)
*A61B 5/00* (2006.01)

(52) U.S. Cl.
CPC ........ *A61B 5/04012* (2013.01); *A61B 5/0478* (2013.01); *A61B 5/6817* (2013.01); *A61B 5/725* (2013.01); *A61B 2562/0214* (2013.01)

(58) Field of Classification Search
CPC ... A61B 5/6815; A61B 5/6817; A61B 5/0476; A61B 5/0478; A61B 2562/0214
USPC .......................................................... 600/379
See application file for complete search history.

(56) References Cited

U.S. PATENT DOCUMENTS

| 6,093,158 A * | 7/2000 | Morris ..................... A61B 5/11 600/590 |
| 2004/0073104 A1* | 4/2004 | Brun del Re ........ A61B 5/0408 600/372 |
| 2004/0138723 A1* | 7/2004 | Malick ................. H04R 25/552 607/57 |

(Continued)

FOREIGN PATENT DOCUMENTS

| GB | 2353594 A | 2/2001 |
| JP | 2002-52000 | 2/2002 |

(Continued)

OTHER PUBLICATIONS

Normann, "Driven Shields or Guard Rings" in Principles of Bioinstrumentation, Wiley, pp. 193-194 (1988).*

(Continued)

*Primary Examiner* — Lee S Cohen
*Assistant Examiner* — Erin M Cardinal
(74) *Attorney, Agent, or Firm* — Sughrue Mion, PLLC (57) ABSTRACT

A wearable EEG monitor for continuously monitoring the EEG of a user through capacitive coupling to an ear canal of a user comprises an ear insert (1) for positioning within the human ear canal, comprising at least two capacitive electrodes (16) for recording a signal. The electrodes are coated with a dielectricum for electrical insulation. The electrodes are connected to an amplifier (17). The amplifier has an input impedance matched to the impedance of the electrodes. The invention further provides a method of monitoring brain waves.

15 Claims, 10 Drawing Sheets

(56) References Cited

U.S. PATENT DOCUMENTS

| | | | |
|---|---|---|---|
| 2008/0139953 A1* | 6/2008 | Baker | A61B 5/0006 600/509 |
| 2008/0146890 A1* | 6/2008 | LeBoeuf | A61B 5/0059 600/300 |
| 2008/0146892 A1* | 6/2008 | LeBoeuf | A61B 5/11 600/300 |
| 2010/0217098 A1* | 8/2010 | LeBoeuf | A61B 5/00 600/301 |
| 2012/0203077 A1* | 8/2012 | He | A61B 5/02055 600/301 |
| 2012/0209101 A1* | 8/2012 | Kidmose | A61B 5/0478 600/379 |
| 2012/0316418 A1* | 12/2012 | Kilsgaard | A61B 5/0476 600/379 |
| 2013/0131519 A1* | 5/2013 | LeBoeuf | A61B 5/0077 600/476 |
| 2013/0315425 A1* | 11/2013 | Lunner | H04R 25/00 381/323 |
| 2014/0369537 A1* | 12/2014 | Pontoppidan | H04R 25/00 381/314 |

FOREIGN PATENT DOCUMENTS

| | | |
|---|---|---|
| JP | 2009-534108 A | 9/2009 |
| WO | 2006/047874 A1 | 5/2006 |
| WO | 2008/054511 A2 | 5/2008 |
| WO | 2011/000383 A1 | 1/2011 |

OTHER PUBLICATIONS

Kugelstadt, "Auto-zero Amplifiers Ease the Design of High-Precision Circuits" Analog Applications Journal 2Q pp. 19-27 (2005).*

International Search Report for PCT/EP2011/064544 dated Apr. 27, 2012.

Communication dated Mar. 3, 2015, issued by the Japanese Intellectual Property Office in counterpart Japanese Patent Application No. 2014-525329 with English translation.

* cited by examiner

EEG MONITOR WITH CAPACITIVE ELECTRODES AND A METHOD OF MONITORING BRAIN WAVES

CROSS REFERENCE TO RELATED APPLICATIONS

The present application is a continuation-in-part of International application No. PCT/EP2011064544, filed on Aug. 24, 2011, published as WO-A1-2013026481, and incorporated by reference herein in its entirety.

BACKGROUND OF THE INVENTION

1. Field of the Invention

The invention relates to an EEG monitor. The invention, more specifically, relates to a wearable EEG monitor adapted for continuously monitoring the EEG response of a user. The invention further provides a method of monitoring brain waves.

2. The Prior Art

It is generally known, particularly within medical science, to investigate brain waves by placing electrodes on the scalp of a subject, whose brain waves is desired to measure, processing and interpreting the detected brain waves using suitable equipment. Typically, such equipment is an electroencephalograph, by means of which a so-called electroencephalogram (EEG) may be achieved. Such an EEG provides a measurement and recording of electrical activity in a subject's brain obtained by measuring the electric potential generated on the surface of the subject's scalp by currents flowing between synapses in the subject's brain. Within medical science EEG's are used for various diagnostic purposes.

A system for such a use is known from WO-A1-2006/047874, which describes measurement of brain waves by use of electrodes placed in connection with at least one of the ears of the subject, i.e. placed on an outer ear part or placed in the ear canal. The measurements are used particularly for detecting the onset of an epileptic seizure. WO-A1-2006/047874 also describes the use of electrodes in pairs, as detection and reference electrodes respectively, such a setup being well known in the field of electroencephalography.

Many known systems, like an electrode cap, use electrochemical electrodes with a conductive gel. The need for a conductive gel makes such systems rather unattractive to use in public, because the conductive gel is greasy and not confined to the area covered by the electrode. Furthermore the conductive gel is likely to short-circuit the electrodes, if they are placed in close proximity of each other. Therefore these known systems need spacing between the electrodes, leading to a large and bulky device for monitoring the EEG.

Another disadvantage of known electrochemical EEG electrode is the difficulty in creating a reliable conductive pathway from the skin of the user, to the electrode. Even when using a conductive gel, the electrical path may still be poor, due to the moist, dirt and hair at the skin of the user. This is especially a problem when the monitor is to be used for longer periods of time, where the user is active and is subjected to a non-laboratory environment, i.e. dirt, moist etc.

The known systems for measuring brain waves are generally complicated to use and require qualified personnel to operate, or require surgery to place the electrodes, and even when placed properly, there are still large variations in the recorded EEG, due to variations in the electrical coupling. Furthermore, some systems require large amounts of power to charge the input transistors of the amplifier. Despite the potential in continuous surveillance of users' EEG response in many different areas of medicine and physical science, the systems known are confined to laboratory use.

SUMMARY OF THE INVENTION

The invention, in a first aspect, provides an EEG monitor for continuously monitoring the EEG of a user through capacitive coupling to an ear canal of a user, said EEG monitor comprising at least two capacitive electrodes adapted for recording a signal, the electrodes being coated with a dielectricum for electrical isolation of the electrode, an amplifier connected to the electrodes for amplification of the electrode signals, wherein the amplifier has an input impedance matched to the impedance of the electrodes, and an ear insert for positioning within the human ear canal, at least one of said electrodes being placed at said ear insert.

The proposed ear insert is easy to use and can be used on a day-to-day basis. Because the proposed system uses electrodes that couple capacitively with the skin, the variations in electrical connection are reduced. The ear insert can be placed in the ear by the user, without help from trained personnel. The ear insert furthermore has the advantage that it can operate on batteries or another small independent power source, as it uses approximately 1 mW.

The ear insert records the EEG of the user. By use of advanced statistics and machine learning techniques, abnormalities or specific changes in patterns in the EEG can be characterized. This may be used for monitoring or determining neurologic disorders, or neurogenerative diseases, and this can be used for e.g. warning a person or a relative about an impending epilepsy seizure, a hypoglycemic attack etc.

The ear insert may further be used for improving the treatment of dementia, by tracking specific changes in the EEG. Other areas of use is diagnosis and rehabilitation of sleep disorders, prevention, rehabilitation and treatment evaluation of psychiatric and emotional disorders, fatigue detection, and as part of a brain-computer-interface.

The connection between the electrodes and the amplifier comprises a signal wire and a shield.

The amplifier may be located within the ear insert.

The amplifier may be an Auto-Zero-Amplifier having a high input impedance, such that the corner frequency may be as low as 1 Hz.

The amplifier may comprise a sample-and-hold circuit for keeping the shield at a potential close to that of the signal wire.

The ear insert may comprise a test circuit for testing the capacitive connection, having a signal generator for generating a signal with a frequency outside the frequency range intended to measure.

The ear insert may comprise a signal processor which may be located at a behind-the-ear device comprising the battery or other power supply means.

The ear insert may be made of a flexible material that adapts to the shape of the ear canal.

The electrodes may be fixed to an inner non-flexible part of the ear insert, covered with an outer flexible part, which conforms to the shape of the ear canal. A reference electrode can be located outside the ear canal, e.g. in the concha or at the skull next to the ear.

The electrodes are in an embodiment distributed evenly over the circumference of the ear insert.

In an embodiment the electrode is double curved, thus conforming better to the shape of the ear canal.

The invention, in a second aspect, provides a method of monitoring brain waves comprising arranging a capacitive electrode coated with a dielectricum in an ear insert, placing the ear insert within an ear canal of a human subject, arranging at least one reference electrode coated with a dielectricum in contact with the head of the subject, placing a processor adjacent the electrode of the subject, connecting the electrodes to the processor, and using the processor to record and process the signals from the electrodes thereby monitoring the brain waves.

The invention is pertinent for providing a wearable EEG monitor for long-term continuous, non-invasive monitoring of a user with a minimum of use of extensive and complicated equipment, which may be used in an uncomplicated way in everyday life outside a clinical and a laboratory environment, while obtaining high quality EEG responses from the user of the monitor.

The capacitive electrodes are connected to an amplifier for amplification of the EEG response and further to a signal processor, for interpretation of the recorded EEG, and to a further storage means, for storing the recorded EEG. The interpretation is based on advanced statistic and machine learning techniques.

In the present context an electrode is meant to encompass a capacitive electrode, i.e. an electrode that does not require a galvanic contact, nor electrical current running between the electrode and the skin of the user. Capacitive electrodes may be implemented in a ear insert for picking up the EEG response through capacitive coupling to the skin of the ear canal.

BRIEF DESCRIPTION OF THE DRAWINGS

The invention will now be described in more detail in respect to the drawings, where.

DETAILED DESCRIPTION OF THE INVENTION

Figure 1:
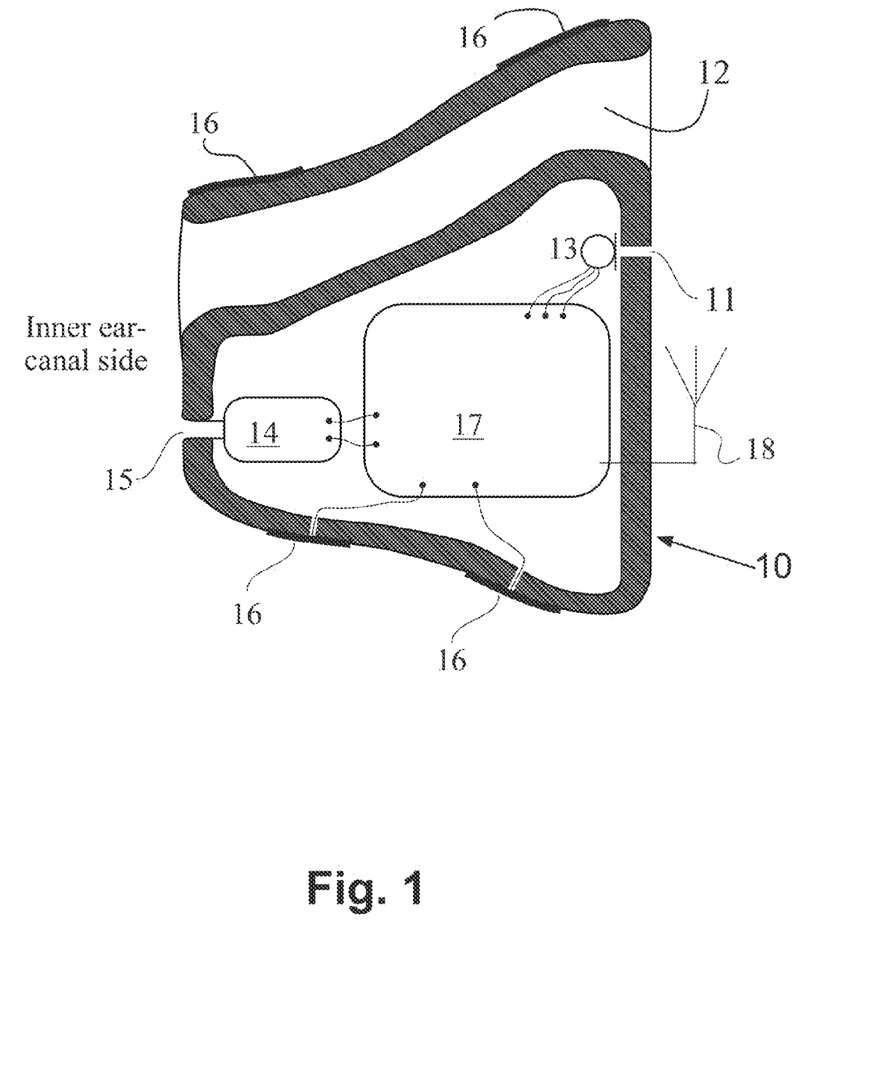
FIG. 1 is an ear insert with capacitive electrodes for picking up an EEG response of the user.

FIG. 1 shows an ear insert 10, having capacitive electrodes 16. The ear insert comprises a ventilation channel 12, adapted to ensure that the ear insert does not occlude the ear of the user. The ear insert further comprises an electronic module 17 connected to the capacitive electrodes 16 for amplification of the EEG response. Furthermore, it may be beneficial to have a microphone inlet 11, a microphone 13, a loudspeaker 14 and a sound outlet 15 within the ear insert, to ensure that the user is able to hear sounds coming from the surroundings. The microphone and loudspeaker are connected to the electronic module 17. The electronic module may further have means for amplification of the sound.

In some situations, it is beneficial that the ear insert is adapted for communication with other devices, e.g. an ear insert at the contralateral ear or a remote control. The ear insert therefore also comprises an antenna 18 and a radio transceiver (not shown) for wireless communication. The antenna may be used for transmitting EEG recordings made at one ear insert to the contralateral ear insert, for enabling comparing the EEG recording within the contralateral EEG recording. This is beneficial because synchronization of the recorded EEG from different regions of the brain will enhance the statistical results.

Figure 2:
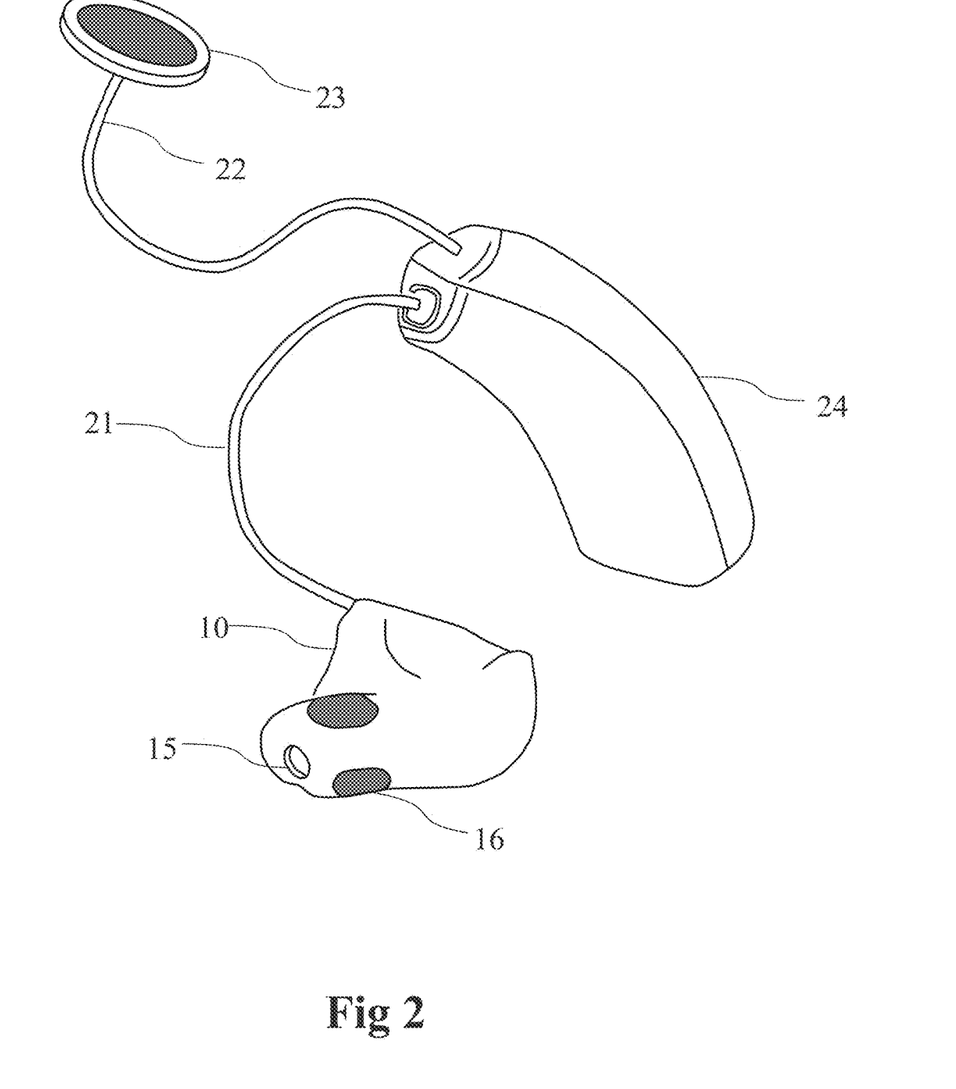
FIG. 2 is an ear insert according to FIG. 1, further comprising a BTE device.

FIG. 2 is an ear insert according to FIG. 1, having capacitive electrodes 16 and a sound outlet 15, and further comprising a Behind-The-Ear (BTE) device 24, adapted for accommodating further electronics (not shown), a battery (not shown), and a digital signal processor (not shown). The BTE device 24 is connected to the ear insert via electrical wires 21, however, the two units may also be adapted to communicate wirelessly. In the embodiment shown, there is a further capacitive pad electrode 23 connected via a wire 22, for placement adjacent to the pinna, or at a location farther from the ear. Such external electrode may also be located at the housing of the BTE device 24, to increase the performance, by increasing the distance between the electrodes and by increasing the reliability.

Figure 3:
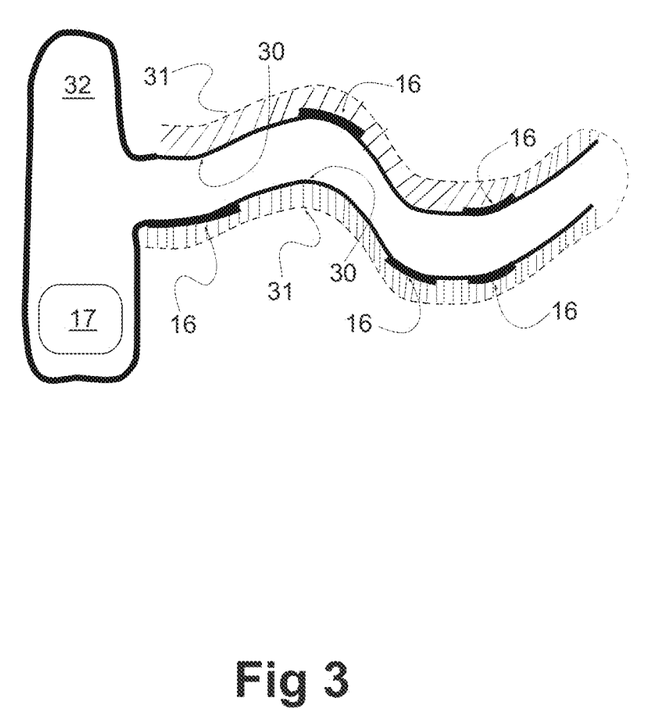
FIG. 3 is an ear insert having a preshaped inner tube comprising electrodes and a soft outer part.

FIG. 3 is an ear insert, having an inner tube 30 preshaped to match the longitudinal shape of the ear canal and comprising capacitive electrodes 16. The inner tube 30 is preshaped such that it fits the bends and curves of the ear canal of the specific user, while having an outer diameter of the inner tube smaller than the diameter of the ear canal. The ear insert further comprises a dielectric outer material 31, softer than the rigid tube, of e.g. silicone, foam or rubber that enables the ear insert to fit tight to the ear canal, without excessive pressure on the skin. The electrodes 16 are mounted on the inner rigid tube, preferably at the fulcrums of the inner tube, i.e. the points of the ear insert, that support the insert the most and where the distance between the electrode and the skin of the user is foreseen to be minimal and hereby most likely to create a close coupling to the skin through the dielectric material 31. The ear insert further comprises an outer part 32 located at the concha of the user, where the electronic module 17 is located. The electrodes are connected (not shown) to the electronic module for amplification and analysis of the EEG response picked up from the user.

Figure 4:
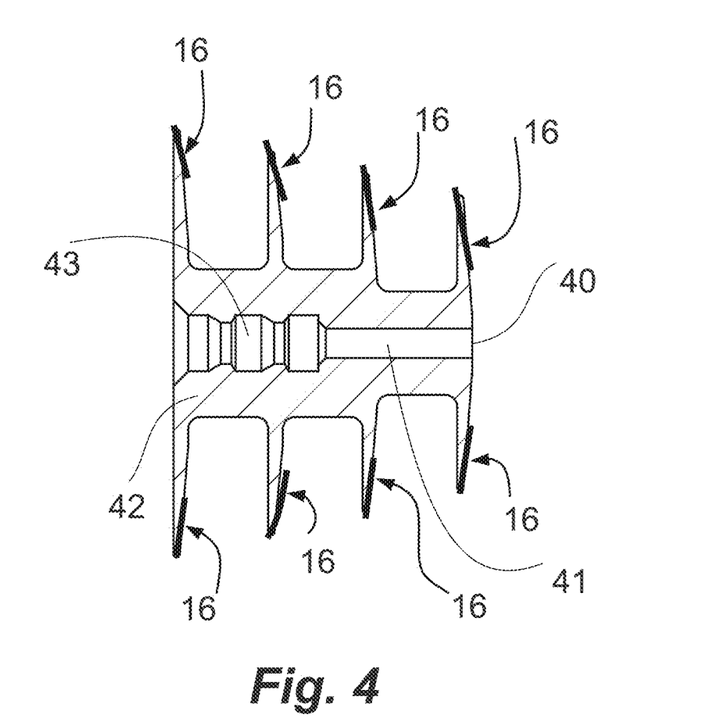
FIG. 4 is an ear insert comprising several flanges with capacitive electrodes.

FIG. 4 shows a cross section of the ear insert 40 with capacitive electrodes 16. The ear insert comprises a sound channel 41, for ventilation and transmittal of sound to the ear drum of the user. The sound channel 41 is rigid to always allow free passage in and out of the ear canal. The sound channel 41 may vary in diameter, e.g. with bulges 43, to shape the frequency response of the channel 41. The material 42 surrounding the sound channel is flexible so as to conform to the shape of the ear canal of the user. The ear insert has flanges or rims comprising capacitive electrodes 16, the flanges extending outward from the sound channel. Upon insertion of the ear insert into the ear canal, the flanges bend backward towards the outside of the ear canal, whereby the capacitive electrodes 16, including a dielectricum (not shown), are forced against the skin of the ear canal. Ensuring a minimal distance between the capacitive electrode 16 and the skin optimizes the capacitive coupling between the electrode 16 and the skin. The flanges may be circumferential or extend outward in several directions perpendicular to the sound channel 41. In the circumferential embodiment, each flange preferably comprises several electrodes spaced apart. The electronics may be located within the ear insert (not shown) or in a behind-the-ear device (not shown).

Figure 5A:
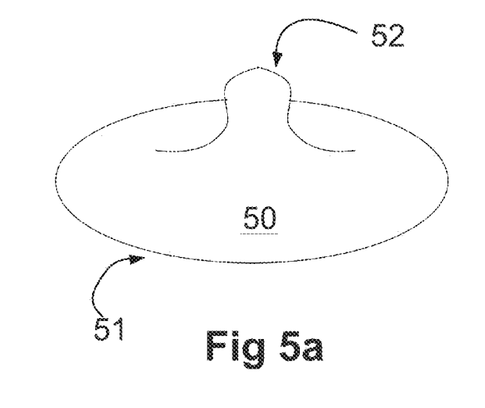
FIG. 5a is an electrode for use in an ear insert.

FIG. 5*a* shows an electrode 50 having a base plate 51 and an electrode salient 52 protruding out from the base plate 51. The electrode 50 substantially has the shape of a bowler.

Figure 5B:
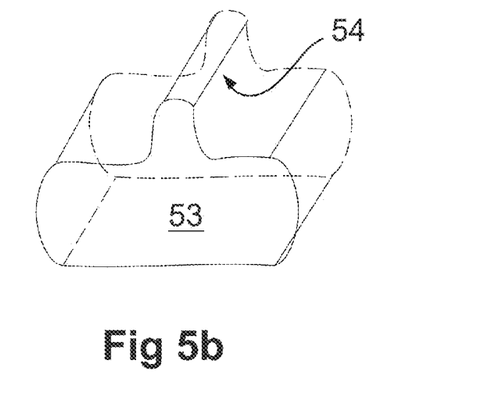
FIG. 5b is another electrode for use in an ear insert.

FIG. 5*b* shows an elongate electrode 53, where an electrode salient 54 is protruding out from the body of the electrode. Both the electrode salient and the electrode body have an elongate shape. The advantage of the elongated electrode over the electrode of FIG. 5*a*, is that the elongated electrode has a larger contact area, where it is in contact with the skin and therefore has a higher capacitance than the bowler hat type electrode of FIG. 5*a*.

Figure 5C:
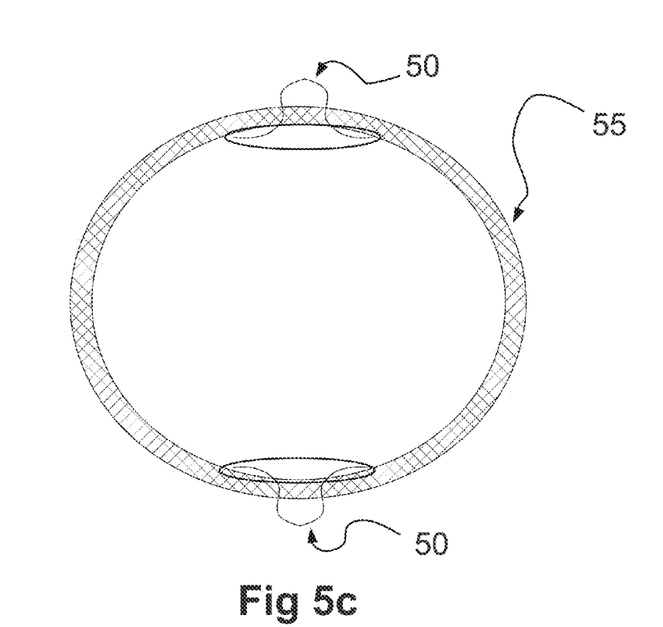
FIG. 5c is an ear insert comprising an electrode as shown in FIG. 5a or 5b.

FIG. 5*c* shows a cross section of an ear insert comprising an electrode according to FIG. 5*a* or 5*b*. The ear insert is made of an elastic material, which is able to conform to the shape of the ear canal, but still being resilient enough to create a sufficient force, to press the electrode 50 out against the skin of the ear canal. The electrode is extending out through the ear insert. The pick-up salient of the electrode, whether it is a bowler electrode or an elongate electrode, is penetrating the material 55 of the ear insert, so as to extend out through the outer circumference of the ear insert, optimizing the distance to the skin of the ear canal.

Figure 6A:
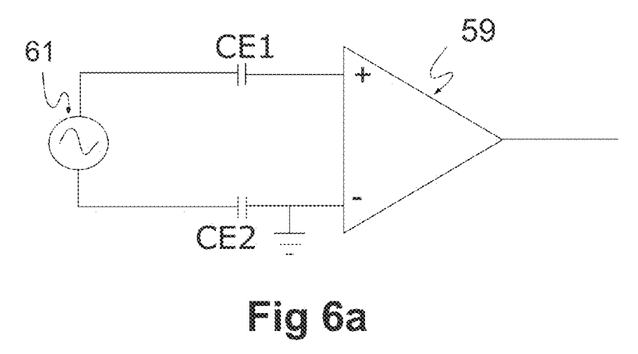
FIG. 6a is a diagram of the operational amplifier and the capacitive electrode for picking up an EEG response.

FIG. 6*a* shows two capacitive electrodes CE1 and CE2, an EEG generator 61 and an operational amplifier block 59. The operational amplifier block 59 amplifies the voltage difference between the two electrodes CE1 and CE2. By grounding one terminal of the amplifier, the amplifier is connected as a single ended amplifier and the equivalent capacitance of the electrode C may be computed as the serial capacitance of the two electrodes CE1 and CE2 when placed on the skin of the user, $$C = \frac{CE1 \cdot CE2}{CE1 + CE2}.$$

Figure 6B:
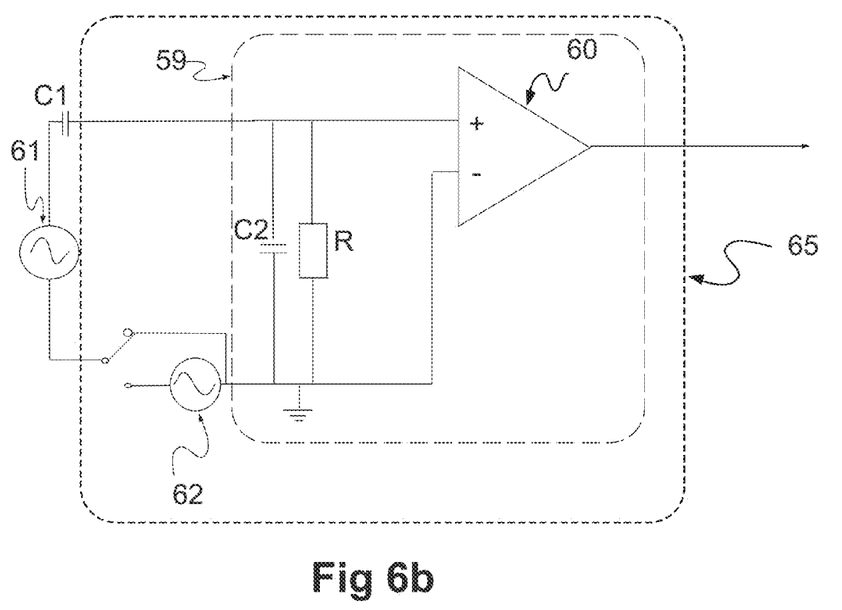
FIG. 6b is an equivalence diagram of the amplifier in FIG. 6a, determining the lower cut-off frequency.

FIG. 6*b* is an electrical diagram of an amplifier connected to a capacitor C1, which is an equivalent of the two electrodes CE1 and CE2 in series. The amplifier is part of the electronics module 17 of FIG. 1. The diagram comprises an EEG generator 61 which equivalents the EEG response of the user, the EEG response being coupled capacitively via the capacitor C1, wherein the one electrode plate is the skin of the user and the other electrode plate is the electrode plate of the capacitive electrode. Between the electrode plate and the skin of the user is a dielectricum, making the electrode couple capacitively to the skin. The block 65 is the electrical circuit for amplification of the signal generated by the EEG generator 61. The capacitor C2 in parallel with the electrode is approximately ⅒ of the capacitance of the electrode C1, hereby creating a voltage divider of one to ten between the two capacitors C1 and C2, in this way, approximately 10% of the voltage from the EEG potential is distributed across the capacitor C1, whereby 90% is available for the operational amplifier 60. Reference 59 designates the amplifier block, comprising the parasitic components C2 and R and the amplifier 60. C2 and R may be chosen appropriately when designing the amplifier block 59.

The sizes of the electrode plates are limited due to the physical size of the ear canal and hereby the surface of the ear insert, consequently the capacitance of the electrode is limited, due to the small electrode capacitance. The impedance of the amplifier should be kept high. The frequency characteristic of the matching circuit should present a high-pass filter having a cut off frequency of approximately 1 Hz.

The operational amplifier block 59 is a suitable low noise amplifier and is connected to each side of the EEG generator 61, i.e. an electrode pair to amplify the difference in potential between the two electrodes 16 (ref. FIG. 1). In order to test the electrode 16, generator 62 can be enabled, generating a test signal at e.g. 30 Hz. A 30 Hz signal is above typical EEG signals of 1 to 10 Hz, and a 30 Hz test signal is therefore easily recognizable outside the EEG signal range. The response to the test signal will give a clear indication of how well the electrodes couple to the skin. The capacitance of C1 depends on the actual sizes of the electrodes and the distances to the skin, i.e. the coupling will vary from user to user and from day to day, e.g. one day the distance between the electrode and the skin may be 0.4 mm, and the next day, the distance may be 0.3 mm. The size and shape of the ear canal changes when moving the jaw, e.g. by chewing, but will in most cases be in the range of 1 to 10 pF. A suitable parallel capacitor is then ⅒ of C1 i.e. 100 to 1000 fF.

Figure 7:
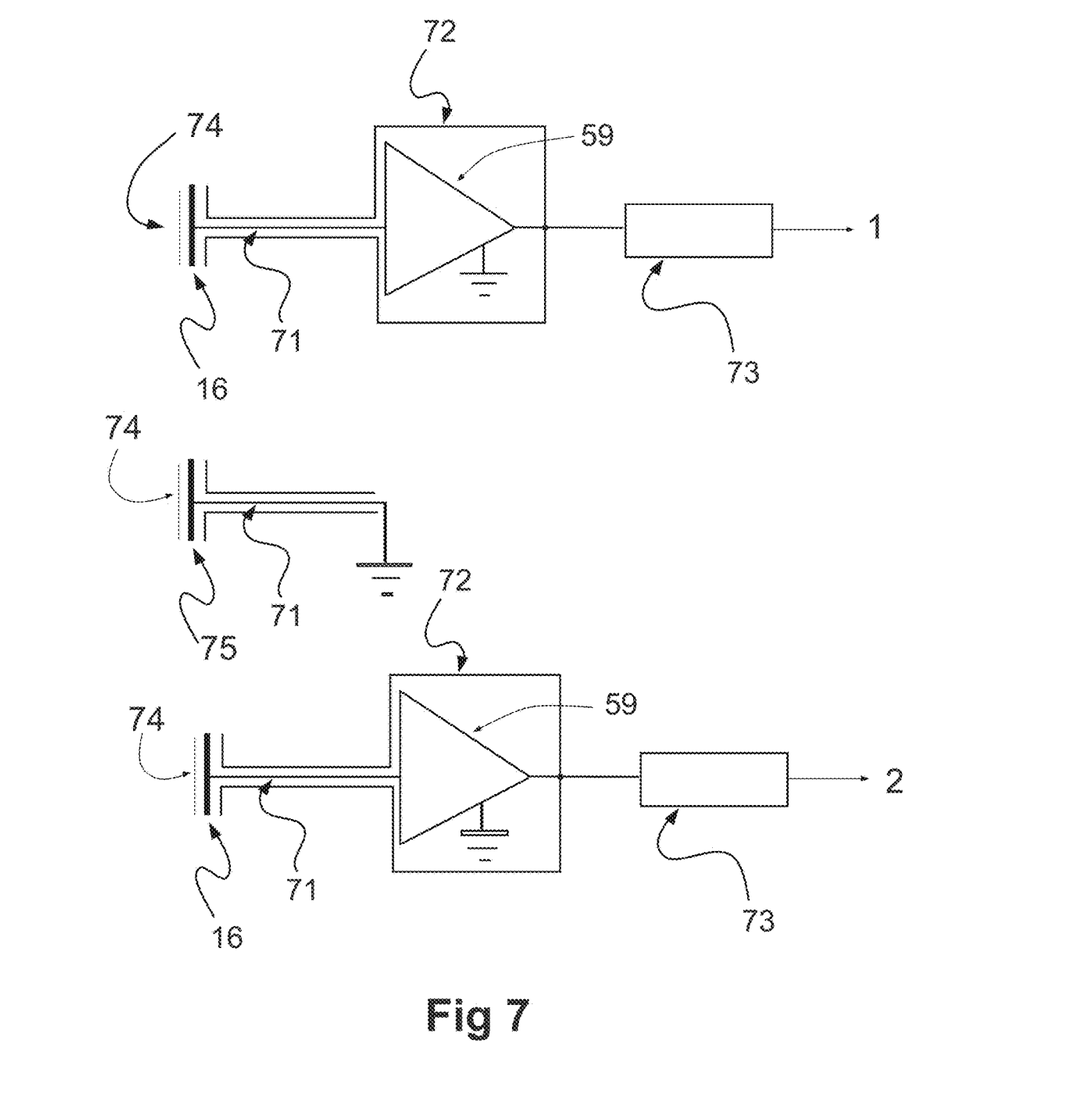
FIG. 7 is an electrode with an operational amplifier and an analogue-to-digital converter.

FIG. 7 shows a number of electrodes 16, 75, connected to low noise amplifier block 59 via a wire or lead 71 having a shield 72, for shielding the signal wire against interfering electrical coupling, and analogue-to-digital converter (ADC) 73, converting the recorded EEG into digital signals. The electrode 16 is connected to the low noise amplifier (LNA) block 59 via a shielded cable such as a coax cable comprising a signal line 71 and a shield 72. The amplifier is connected to a reference electrode 75, to permit amplification of the EEG signal relative to the reference signal from reference electrode 75. The amplifier signal is transmitted to an analogue-to-digital converter 73. Several electrodes may be arranged with respective analogue-to-digital converters, the outputs from respective A/D converters being fed to the digital signal processor as channel one, channel two and so forth. The electrode 16 further comprises a dielectric material 74 covering the electrode 16 to ensure a capacitive coupling to the skin of the user. The shield 72 is coupled to the output of the LNA. By connecting the shield to the output of the amplifier, the shield has the same potential as the signal wire and consequently there is no difference of potential between the signal wire and the shield.

Figure 8:
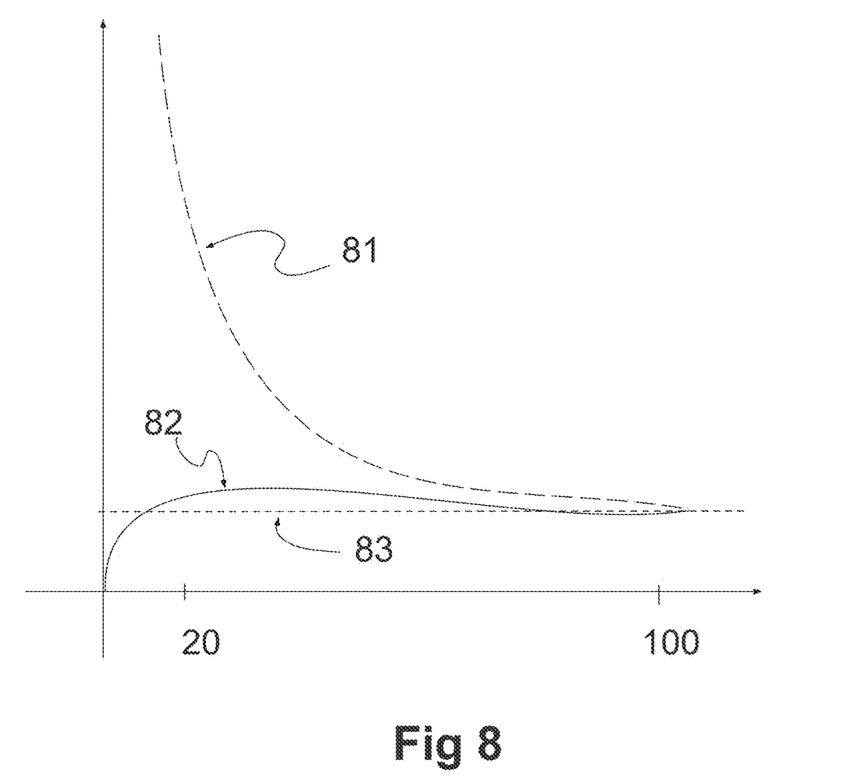
FIG. 8 is a graph depicting the 1/f noise for a traditional operational amplifier versus an Auto Zero Amplifier, and the acceptable noise level at 100 nV/√Hz.

FIG. 8 shows the 1/f noise of a traditional operational amplifier 81 and of an Auto Zero Amplifier (AZA, to be explained in context with FIG. 10) 82, together with the acceptable noise level 83 at around $$\frac{100 \text{ nV}}{\sqrt{\text{Hz}}}.$$

AZA amplifiers are more suitable than traditional amplifiers, because AZA amplifiers have a lower noise level at low frequencies, where EEG signals occur.

Figure 9:
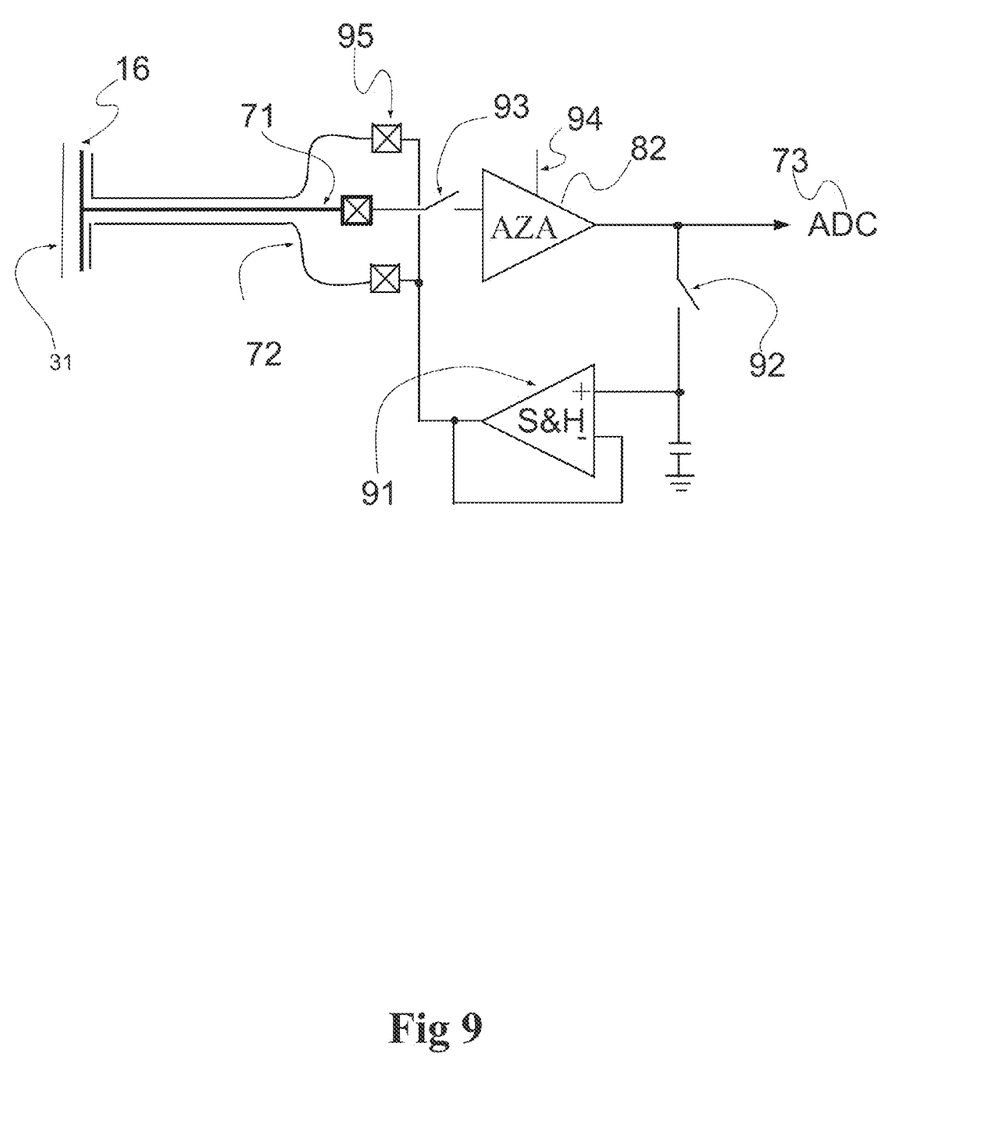
FIG. 9 is an Auto Zero Amplifier (AZA) suitable for amplification of EEG signals in a system according to an embodiment of the invention.

FIG. 9 shows an amplifier arrangement for a wearable EEG monitor comprising an electrode 16 with a dielectric material 31 covering the electrode 16, an AZA amplifier 82 connected to the electrode via a wire 71, having a shield 72.

The output from the AZA 82 is fed to an analogue-to-digital converter (ADC) 73 and further fed back to the wire shield 72 via a sample-and-hold (S&H) circuit 91, to generate the potential to the shield 72, whereby the shield obtains the same signal potential as the input at electrode 16 and wire 71. The sample & hold circuit, also known as a follow & hold or track & hold circuit, captures the voltage of the output from the AZA and freezes its value to the output. By matching the two potentials, there is no, or minimal, voltage between the wire and the shield, and the capacitive effect between the signal wire and the shield is hereby minimized. The switches 92 and 93 and clock input 94 are synchronized and controlled by a clock generator (not shown). Reference 95 designates a chip pad for connecting the amplifier, which is part of a more complex chip design, to the electrode.

Figure 10:
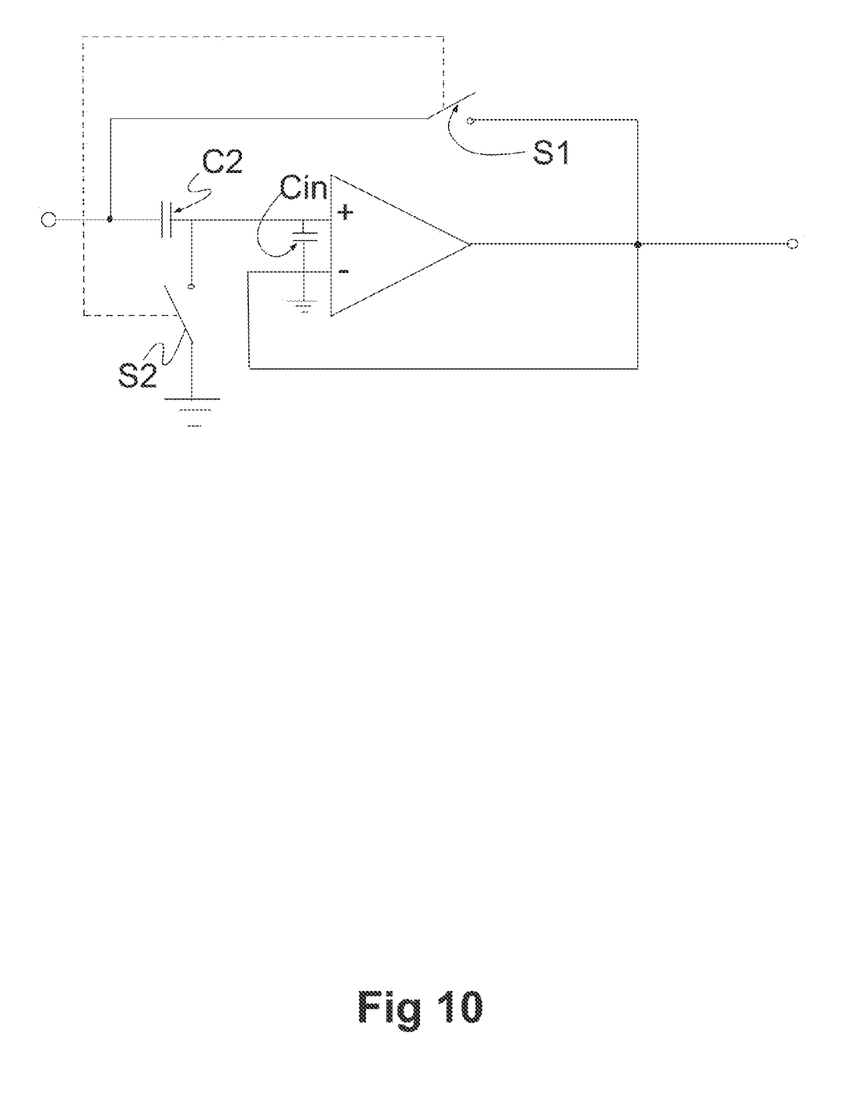
FIG. 10 is an example of the auto-zero amplifier.

FIG. 10 shows an example of an Auto-Zero Amplifier. It operates in two phases: a zero phase (S1 and S2 are on) and an amplification phase (S1 and S2 are off). The gain is one and has an equivalent input impedance which is related to the switching frequency of S1 and S2 and the input capacitance of the amplifier. We may choose a switching frequency, $f_s$=200 Hz. Looking at signals in the range of 1-10 Hz or 1-20 Hz, a 200 Hz switching frequency is adequate according to the Nyquist theorem. Suitable amplifiers can be designed having an input capacitance of $C_{in}$=100 fF. This results in:

$$R = \frac{1}{C_{in} f_s} = \frac{1}{100 \cdot 10^{-15} \cdot 200} = 50 \text{ G}\Omega$$

The cut off frequency, $f_n$, of the system can be found according to FIG. 6b. In this figure, R represents the input impedance of the amplifier, C2 is the capacitance of the input pad and various parasitic capacitances, and C1 is the electrode capacitance. Below C2 is set to 500 fF.

$$f_n = \frac{1}{2\pi R(C_{electrode} + C_{pad})} = \frac{1}{2\pi \cdot 50 \cdot 10^{-9}(6.5 \cdot 10^{-12} + 0.5 \cdot 10^{-12})} = 0.45 \text{ Hz}$$

This gives a noise corner frequency of 0.45 Hz, i.e. well below the frequency for recording EEG, usually in the range 1 to 10 Hz.

Due to C1 and C2, the voltage at the input of the low noise amplifier is 93% of the EEG voltage for frequencies above 1 Hz.

The dielectricum ensures that no current is running in the crossover between the skin and the electrode, however it should also be as thin as possible, because the capacitance is inversely proportional to the distance between the electrodes, $$C = \frac{A * \varepsilon}{d},$$

where C is the capacitance, A is the area, $\in$ is the dielectric constant of the dielectric material, and d is the distance between the electrode and the skin. The dielectricum may be chosen among a number of different materials, such as silicon oxide, aluminum oxide, polyamide (nylon), PTFE (polytetrafluoroethylene or Teflon), etc.

The size of the electrodes is a trade off between the option to fit several electrodes within a confined space, and the capacitance of the electrode, which is proportional to the area, pointing to large electrode sizes. A preferable size is between 5 mm$^2$ and 100 mm$^2$. The electrode may be flexible but is preferably preshaped in a double curved shape to best fit the area of the ear, where it is to be placed. The monitoring device has several electrodes, where each one of them may have an individual shape, to best fit that particular area, where it is supposed to fit the user.

The ear insert may have many different shapes, the common goal for all shapes being, to have an ear insert that gives a close fit to the user's skin and is comfortable to wear, meaning that it should occlude the ear as little as possible.

In one embodiment the ear insert has a customized shape for the ear canal of the user. The ear insert is a hollow shell and is made for the specific ear canal according to an imprint of the ear canal. The electrodes may be mounted on the inside or outside of the hollow shell. If mounted on the inside of the shell, the shell itself may be sufficient dielectric to ensure pure capacitive coupling. Furthermore mounting the electrodes on the inside of a shell makes wiring of the electronic easier, than does outside mounting of the electrodes.

In another embodiment, the ear insert comprises a pipe, where the electrodes may be mounted on the inner or outer circumference of the pipe. The pipe is made in different diameters, as to best fit the diameter of the ear canal. The pipe can also be shaped to fit the shape of the ear canal in the longitudinal direction. On the outer circumference the pipe is covered with a soft and flexible material like silicone, foam, rubber or another soft material that ensures a secure and comfortable fit for the user.

In another embodiment, the ear insert is in the form of a stent. Stents have the advantage that they are flexible, in the way that they can be inserted into the ear canal in a contracted state, and then released to form a close fitting ear insert. The stent may be a self-expanding metallic stent, which is covered by a dielectricum and hereby form a capacitive electrode, which can be connected to the amplifier and signal processor.

A particular problem with amplifiers for EEG monitoring devices is the low frequency noise of the amplifier, also known as the 1/f noise. EEG signals are low frequency, i.e. typically 1 to 10 Hz, however the noise of typical amplifiers is very high at low frequencies, i.e. with a noise corner frequency in the range at or above 100 Hz or even between 1 to 2 kHz for high speed amplifiers, making these amplifiers unsuitable as EEG signal amplifier. This problem is usually solved by using large transistors having large capacitors at the input of the operational amplifier, but increasing the capacitor size also increases the power consumption of the amplifier. This is however not an option when the whole system has to be carried at or in the ear, and powered by a small battery as known from the hearing aid industry. To keep the power consumption low, it is proposed to use an auto-zero-amplifier or a chopper-stabilized amplifier to amplify the EEG recording.

The electrodes picking up the EEG response of the user are connected to an amplifier, feeding an analogue-to-digital converter, after which the signal is handled by a Digital Signal Processor (DSP). The connection between the electrode and the amplifier is preferably via a shielded wire such as a coax cable. The shield is floating at the electrode end, while the shield is connected to the output of the amplifier at the amplifier end. By connecting the shield to the amplifier output, the potential of the shield is kept high whereby the capacitive coupling between the signal wire and the shield is minimized. In a preferred embodiment, the shield is connected to the operational amplifier via a "sample & hold" amplifier for generating a voltage potential to the shield.

An ear insert according to the proposed invention may be used for continuous monitoring of EEG signals indicative of a medical seizure like hypoglycemia, epilepsy, or similar conditions. The device is used to foresee a seizure by analyzing the EEG signal by a digital signal processor, and notify the user in case the analyzed signal indicates an impending seizure. The signal processor is continuously evaluating the EEG recording with statistical data analysis and machine learning methods.

The signal processor, power supply, microphone, loudspeaker etc. may be located at the ear insert or at a behind-the-ear (BTE) part. Whether these parts are located at the ear insert or in the BTE part depends on the size and shape of the ear canal i.e. whether the ear insert is large enough for accommodating all components.

We claim:

1. An EEG monitor for continuously monitoring the EEG of a user through capacitive coupling to an ear canal of a user, said EEG monitor comprising an ear insert for positioning within the ear canal of the user, and at least two capacitive electrodes arranged in the ear insert and adapted for recording a signal, the electrodes being coated with a dielectricum for electrical isolation of the electrodes, an amplifier connected to the electrodes for amplification of signals recorded by said electrodes, wherein the amplifier has an input impedance matched to an impedance of at least one of the electrodes, and wherein the one electrode is connected to the amplifier via a connection comprising a signal wire and a shield, and said monitor comprising a sample-and-hold circuit holding a potential of the shield close to a potential of the signal wire.

2. The EEG monitor according to claim 1, configured to measure an EEG response represented by the signals recorded by said electrodes.

3. The EEG monitor according to claim 1, wherein the amplifier is located within the ear insert.

4. The EEG monitor according to claim 1, wherein the amplifier is an Auto-Zero-Amplifier.

5. The EEG monitor according to claim 1, wherein the amplifier is a chopper-stabilized amplifier.

6. The EEG monitor according to claim 1, wherein the amplifier has an input characteristic of a high pass filter with a corner frequency at 1 Hz.

7. The EEG monitor according to claim 1, comprising a test circuit for testing said capacitive coupling, having a signal generator for generating a test signal having a frequency outside an expected frequency range of EEG signals.

8. The EEG monitor according to claim 1, wherein the entire monitor is located at an in ear device.

9. The EEG monitor according to claim 1, comprising a behind-the-ear device and a signal processor, located at the behind-the-ear device, for processing signals from said amplifier.

10. The EEG monitor according to claim 9, wherein a power supply is located at the behind-the-ear device.

11. The EEG monitor according to claim 1, wherein the ear insert is made of a flexible material that adapts to the shape of the ear canal.

12. The EEG monitor according to claim 1, wherein the electrodes are fixed to an inner non-flexible part, which is covered with an outer flexible part, which conforms to the shape of the ear canal.

13. The EEG monitor according to claim 1, wherein the electrodes are distributed evenly over the circumference of the ear insert.

14. The EEG monitor according to claim 1, wherein the one electrode has a double curvature shape.

15. A method of monitoring brain waves comprising:
providing the EEG monitor of claim 1,
placing the ear insert within the ear canal of the user,
arranging at least one reference electrode coated with a dielectricum in contact with the head of the user,
placing a processor adjacent the ear of the user,
connecting the electrodes to the processor, where the connection comprises the signal wire and the shield, and
using the processor to record and process the signals recorded by said electrodes thereby monitoring the brain waves.

* * * * *